United States Patent [19]

Kreiskorte

[11] Patent Number: 4,855,678
[45] Date of Patent: * Aug. 8, 1989

[54] APPARATUS FOR GUIDING THE SENSOR HOLDER OF A SURFACE TESTING APPARATUS

[75] Inventor: Heinz Kreiskorte, Dortmund, Fed. Rep. of Germany

[73] Assignee: Thyssen Industrie AG, Essen, Fed. Rep. of Germany

[*] Notice: The portion of the term of this patent subsequent to Jul. 28, 2004 has been disclaimed.

[21] Appl. No.: 905,473

[22] Filed: Sep. 10, 1986

[30] Foreign Application Priority Data

Sep. 13, 1985 [DE] Fed. Rep. of Germany ....... 3532654

[51] Int. Cl.⁴ .................. G01R 33/00; G01B 7/14; G01N 27/72
[52] U.S. Cl. ................... 324/262; 324/207; 324/226; 324/225; 324/227; 269/266; 901/9; 901/19; 901/44; 901/46
[58] Field of Search .............. 324/206–208, 324/217, 218, 225–228, 234–243; 269/265, 266; 901/9, 10, 21–26, 44–46, 50, 19; 73/618

[56] References Cited

U.S. PATENT DOCUMENTS

| | | | |
|---|---|---|---|
| 4,041,379 | 8/1977 | Karlsson | 324/262 X |
| 4,215,310 | 7/1980 | Schwerer, III | 324/225 |
| 4,258,319 | 3/1981 | Shimada et al. | 324/226 |
| 4,314,203 | 2/1982 | Haberlein | 324/262 |
| 4,423,636 | 1/1984 | Plante | 324/262 X |
| 4,528,507 | 7/1985 | Domin et al. | 324/226 X |
| 4,579,271 | 4/1986 | Fujita et al. | 269/266 X |
| 4,596,953 | 6/1986 | Nagasaka et al. | 324/262 X |
| 4,604,574 | 8/1986 | Posluszny et al. | 324/207 |
| 4,641,092 | 2/1987 | Sakamoto et al. | 324/262 X |
| 4,677,578 | 6/1987 | Wright et al. | 324/61 R X |
| 4,682,498 | 7/1987 | Kreiskorte | 73/618 |

FOREIGN PATENT DOCUMENTS

| | | |
|---|---|---|
| 923747 | 1/1955 | Fed. Rep. of Germany . |
| 2458606 | 7/1975 | Fed. Rep. of Germany . |
| 3411854 | 10/1984 | Fed. Rep. of Germany . |
| 711237 | 6/1954 | United Kingdom . |
| 2084735 | 4/1982 | United Kingdom . |

Primary Examiner—Reinhard J. Eisenzopf
Assistant Examiner—Warren S. Edmonds

[57] ABSTRACT

An apparatus by which a sensor holder of a surface testing apparatus can be moved along a preselected path of movement over the surface to be examined. The apparatus has a guide rail establishing the path of movement, which can emulate the contour of the surface and on which the sensor holder is supported.

12 Claims, 4 Drawing Sheets

APPARATUS FOR GUIDING THE SENSOR HOLDER OF A SURFACE TESTING APPARATUS

BACKGROUND OF THE INVENTION

The invention relates to a surface testing apparatus having a sensor holder and an apparatus whereby the sensor holder can be moved along a preselected path of movement over a surface to be tested.

In a known surface testing aparatus of this kind (DE-OS 33 24 444) there is provided a sensor holder which rotates on a circular path about a cylindrical test body. To assure a constant distance between the sensor holder and the surface being tested, a rotating drum bearing the sensor holder can be adjusted in two directions by means of a control system such that it is coaxial with the test body. Such control is effective only if the surface of the test body is actually cylindrical. But if the surface deviates from the cylindrical shape, an adjustment would have to be made at a plurality of points during each rotatioln of the drum, which for practical reasons is impossible at the desired high rotatory speed.

To avoid this disadvantage, the known apparatus has a sensor holder supported on the workpiece surface by an air system, so as to be able to compensate for local variations of the distance by means of the air pressure. Such an air system, however, is disadvantageous if the test bodies, for example, are steel slabs emerging from a continuous casting furnace, which, at time of the surface test, have a temperature of, e.g., 800° to 1000° C. and/or a rough surface. For the result would be that the pressure produced by the air system builds up only irregularly, and keeping the distance between test body and sensor holder constant with sufficient accuracy is impossible. Moreover, the known air system would make it impossible to provide additional control by means of the additionally present control system. Lastly, a similar use of the known surface test apparatus on test bodies having other, substantially flat surfaces, such as flat slabs, would not be very effective, since only the average distance between the sensor holder and the surface could be kept constant by means of the control system, and the remaining maximum deviations from this average would be too great. This applies quite plainly to test bodies such as flat steel slabs having a wavy surface whose contour can vary gradually.

It is, therefore, an object of this invention to improve the surface test apparatus of the kind specified such that no direct spacing regulation of the sensor holder will be necessary.

A further object is to design the surface test apparatus such that hot, rough surfaces will be able to be tested without problems.

Yet another object this invention is to provide an auxiliary supporting surface whose shape is closely adapted to the contour of the surface being tested and which has a preselected distance from the surface being tested.

SUMMARY OF THE INVENTION

For the solution of these problems, the invention is characterized in that the apparatus by means of which the sensor holder can be moved along a preselected path of movement over the surface to be tested has a guiding surface on which the sensor holder is supported, and which establishes the path of movement and can be shaped to emulate the contour of the surface being tested.

The invention offers the advantage that it has a guiding surface which establishes the path of movement of the sensor holder and whose shape is adapted to the contour of the surface being tested. Assuming that the surface contour of the test body does not change in the direction of movement of the sensor holder, a single emulation of this surface by means of the guiding surface will suffice, since the sensor holder is guided in each back-and-forth movement by the guiding surface, and is held by the latter at a preselected distance from the test surface. Local fluctuations in the direction of the back-and-forth movement are harmless as soon as they are once detected and the guiding surface is adjusted accordingly. Lastly, with the additional assumption that the contour of the surface gradually varies lengthwise of the moving test body, it is necessary only to gradually modify the guiding surface accordingly. This is easily possible by means of installed control devices. The claimed surface test apparatus therefore corresponds to all the important requirments that can be expected in practice.

Additional advantageous features of the invention will be found in the subordinate claims.

Brief Description of the Drawings

An embodiment of the invention is represented in the drawings, wherein.

Figure 1:
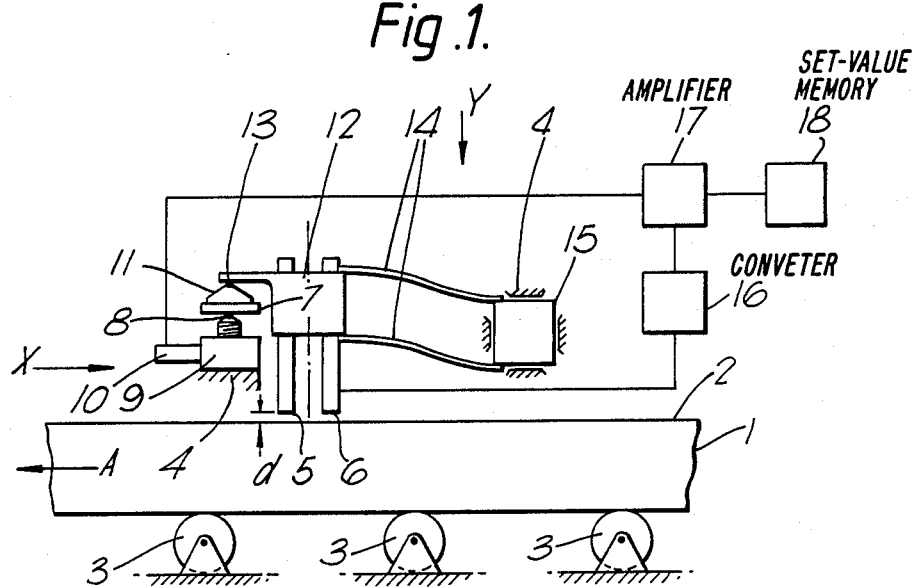
FIG. 1 is a diagrammatic representation of a surface test apparatus seen from the side according to a preferred embodiment of this invention.

According to FIG. 1, a test body 1 is advanced on a set of rollers 3 in the direction of the arrow A. A surface 2 of this test body is to be tested for cracks. For the detection of the cracks a crack sensor 5 is disposed at the distance d above the surface 2 and sends its data to a data processing system not shown. The crack sensor 5 is fastened in a sensor holder 12 which is biased downwardly by two parallel leaf springs 14. The leaf springs 14 are disposed as a parallel guidance system for the sensor holder 12. The sensor holder 12, which is biased downwardly by the leaf springs 14, rests against an upper guiding surface of a guide rail 7 through a swivel joint 13 and a slide 11.

The leaf springs 14 are fastened to a drive beam 15 which is reciprocated perpendicular to the plane of the drawing, FIG. 1. The drive beam 15 is carried in a casing 4 which is represented by the hatched surfaces.

During the reciprocating movement of the drive beam 15, the slide 11 runs back and forth on the guiding surface of the guide rail 7. To enable the crack sensor 5 to be held at a constant distance d from the surface 2, which is important to the operation of the crack sensor 5, the contour of the guide surface 7 is modified according to the invention in order to match the contour of the surface 2.

Figure 2:
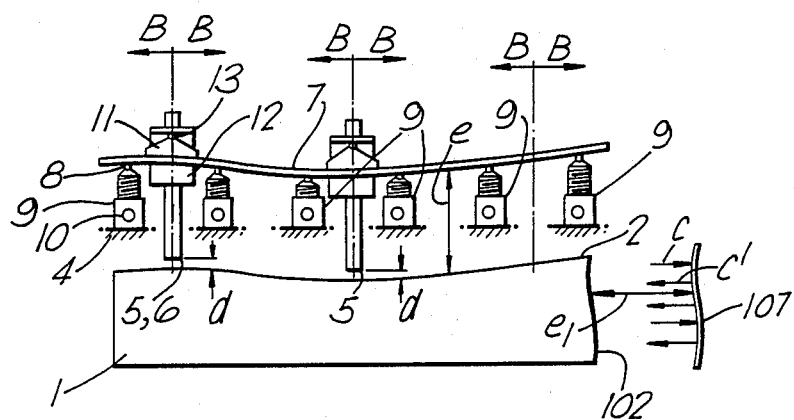
FIG. 2 represents the surface test apparatus according to FIG. 1 as seen in the direction of the arrow X.

For this purpose, the guide rail 7 is in the form of a flexible, preferably resiliently flexible, beam, and is preferably supported, according to FIG. 2, at a plurality of points of support 8 on a like number of actuators which consist, for example, of jacks or lifting gears 9 fastened on the casing 4, which are connected each to a drive 10, e.g., a controllable electric motor. By means of these jacks 9, the guide rail 7 can be elevated or depressed at any of the points of support 8.

As indicated in FIG. 2, the surface can change gradually in the direction of the reciprocating movement of the sensor holder 12 and also in the direction of movement (arrow A in FIG. 1) of the test body 1. Consequently, a distance sensor 6 is additionally contained in the sensor holder 12, and its distance from the surface 2 during the reciprocating movement of the sensor holder 12 is measured whenever it passes one of the points of support 8. The distance sensor 6 can, like the crack sensor 5, consist of an inductive sensor or one operating with eddy currents. Such sensors are generally known (DE-OS 20 44 331, 27 46 618 and 33 24 444, or U.S. Pat. No. 4,258,319).

The signals emitted by the distance sensor 6 are fed to a converter 16 and converted therein to electrical signals which are proportional to the distance of the sensor 6 from the surface 2 and constitute the found or actual values of this distance. These found values are fed to a plurality of controlling amplifiers 17 which are connected each to one of the drivers 10, and in the amplifiers they are compared with set or nominal values which are stored in set-value memories 18. If these found values differ from the set values, the guide rail 7 is raised or lowered in the area of the corresponding point of support 8 by means of the drivers 10 and the jacks 9 until the found values and set values are equal and the distancing of the distance sensor 6 from the surface 2 as the points of support 8 are passed is equal in each case to the particular set value. If all of the set values of the distance are equal, the result will be that the guide rail 7 and its guiding surface will have the same distance from the surface 2 at the locations of all points of support 8 and therefore will have the same contour as the surface 2. Since the distance sensor 6 as well as the crack sensor 5 is fastened to the sensor holder and the latter rides on the guide rail 7, the crack sensor 5 will also be at a constant distance from the surface 2 throughout the pass across the test body.

Figure 3:
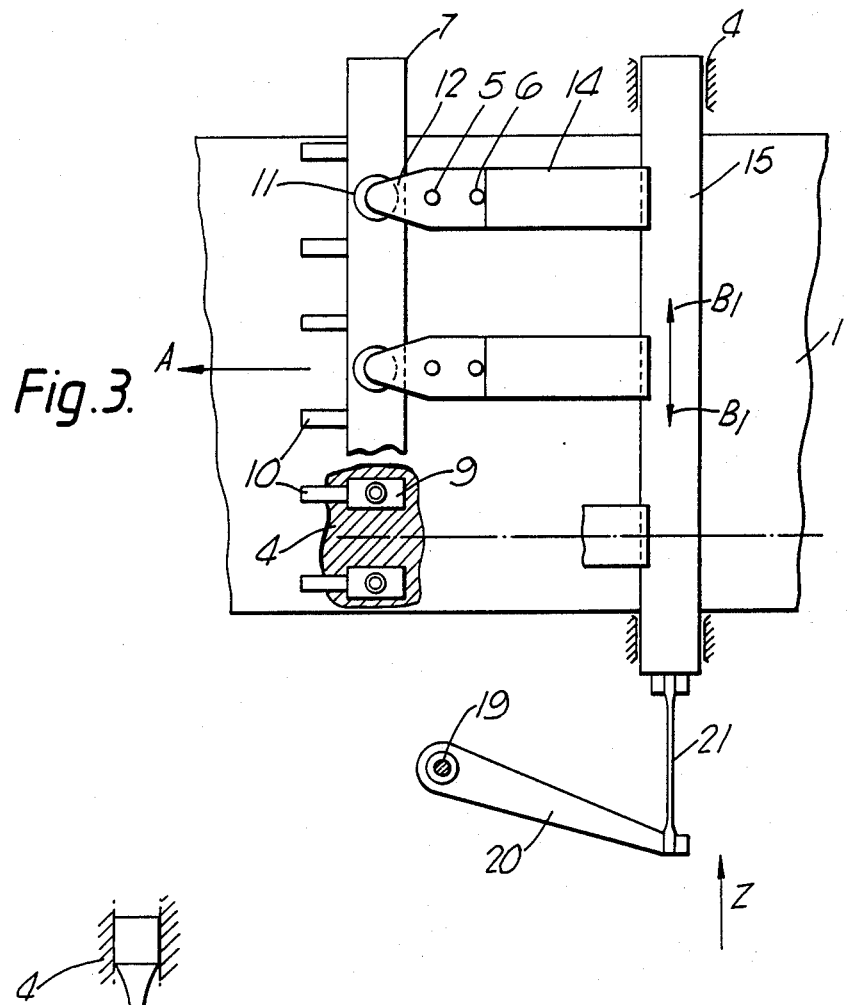
FIG. 3 represents the surface test apparatus according to FIG. 1 as seen in the direction of the arrow Y.

In accordance with FIGS. 2 and 3, provision can be made for supporting a plurality of sensor holders 12 on the guide rail 7 extending across the width of the workpiece 1 and for reciprocating them across only a small section of the width of the test body 1. In this case, each sensor holder 12 is provided with one crack sensosr 5 and one distance sensor 6, and also one combination of parts 8, 9, 10, 13 and 14 is associated with each sensor holder 12, and all pairs of the leaf springs 14 can be fastened to the same drive beam 15. Provision can furthermore be made for selecting the length of the reciprocating movement of the drive beam 15 such that each sensor holder 12 and each distance sensor 6 will, in its reciprocating movement, pass only one or two points of support 8 or a certain number of all of the available points of support. In this case, each distance sensor 6 would be used to measure and control only those points of support 8 which it passes, and for this purpose converters 16 and set-value sources 18 can be associated with each distance sensor 6 or each point of support 8.

In the kind of control described, a distance adjustment is performed only at the points of support 8, so that, between the points of support 8, due to the fine structure of the surface 2, certain departures of the distance between crack sensor 5 and surface 2 from the desired set value can occur.

As an alternative, it would also be possible to determine the distances continuously through the entire duration of the reciprocating movement of the distance sensor 6 and thus to obtain a profile of the distances from the surface 2. Then, with the aid of a data processing system, it would be possible from this distance profile to determine the most favorable positions of all points of support 8 by an optimation process. This optimation process can be programmed so as to minimize the difference between the curve of the guide rail 7 and that of the surface 2.

In FIG. 2, the test body 1 is represented in cross section and has a nonplanar contour on its surface 2 and one lateral surface 102. Upon the lateral movement of the crack sensors 5 in the direction of the arrows B, their distances d from the surface 2 remains constant, since at a distance e above the surface 2 the guide rail 7 is deformed by the jacks 9 such that it largely assumes the contour of the surface 2 of the test body 1. It is desirable to make the dimensions of the guide rail 7 such that the deformation takes place in the elastic range.

The contour of the guide rail 7, conforming to the surface 2, is in the form of a statically indeterminate flexural beam. This contour is more in conformity with the contour of the surface 2 than if the crack sensor 5 would be moved across the entire range of movement along a straight line corresponding to an average distance value. The more precisely the surface 2 is to be simulated, the more points of support 8 are necessary for the guide rail 7. The number of points of support 8 and the number of the crack and/or distance sensors 5 can be independent of one another.

By means of similar systems disposed laterally, it is also possible to emulate the lateral surface contour 102 at a distance e1 by means of an additional guide rail 107, by adapting the latter to the lateral surface, as indicated by the arrows C (FIG. 2).

According to FIG. 3, the drive beam 15 is borne in the casing 4 and can move only in the direction of the arrow $B_1$. The drive system required for the movement is preferably constructed as a vibratory system which consists essentially of a torsion bar 19 and the entire mass of the reciprocated parts of the surface test apparatus. The torque produced by the torsion bar 19 is converted by means of a lever 20 into longitudinal forces which actuate the drive beam 15 through a flexible coupling 21.

Figure 4:
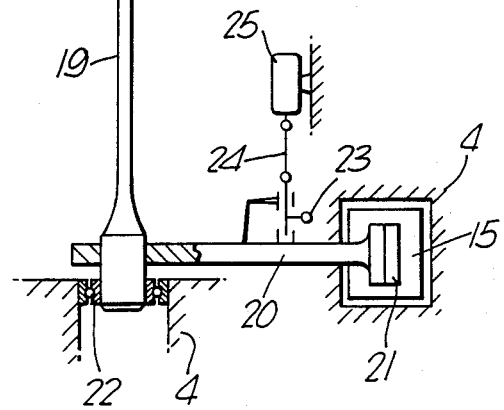
FIG. 4 represents a resonance drive system for the surface test apparatus of FIGS. 1 to 3.

FIG. 4 shows the drive system as seen in the direction of an arrow Z in FIG. 3. The torsion bar 19 serving as an elastic element for the vibratory system is held fixedly at its upper end in the casing 4 and mounted rotatably in a bearing 22 in the housing 4 at its bottom end. The lever 20 is fixedly joined to the torsion bar 19 and can perform an oscillating movement together with the bottom end of the torsion bar 19. This oscillating movement is transferred through the coupling 21 to the drive beam 15 which in turn, as indicated in FIG. 3, moves the sensors 5 and 6 through the leaf springs 14 and the sensor holders 12.

A centrifugal force exciter 23, which is driven through a universal shaft 24 by a controlled-speed motor 25, serves to excite the vibratory system with its natural frequency or with a frequency in the neighborhood thereof. Excitation can also be provided by other systems, such as a pulsating air recoilproducing system or a crack drive, which operates on start-up through a slip clutch. Additional details of the vibratory drive system are described in an earlier application of the same applicant (cf. DE P No. 35 24 106.3 of July 5, 1985 and US-Ser. No. 877 846, June 24, 1986).

On account of the vibration system, the drive can be made substantially smaller than a direct mechanical drive. In the vibratory resonant system, only a small exciter has to be driven, which compensates the damping and friction losses.

To keep the damping and friction losses low, it is proposed to use pneumatic or hydrostatic bearing in the slides 11 and in the mounting of the drive beam 15 in the casing 4, which bearings can be either biased lift-only bearings or full-floating bearings.

Figure 5:
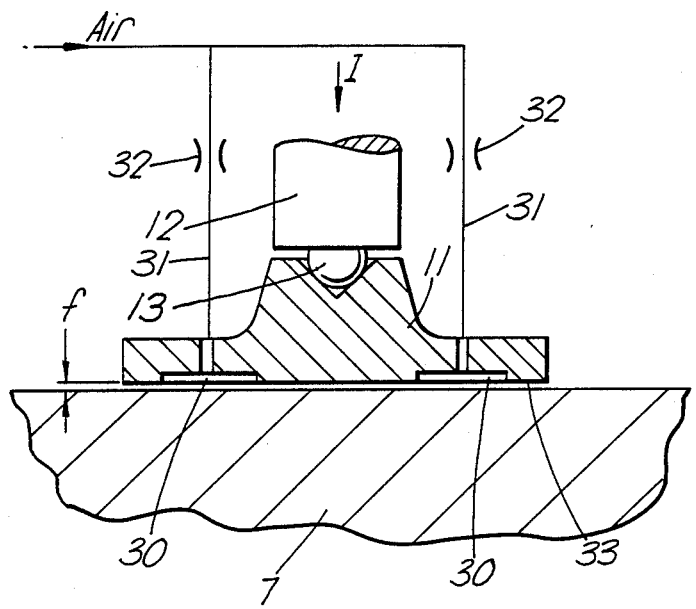
FIG. 5 represents a fluid thrust bearing for the surface test apparatus of FIGS. 1 to 3, FIGS. 6 and 7 represent longitudinal and cross sections through a pneumostatic bearing for the resonance drive system of FIG. 4.

FIG. 5 shows a pneumatic bearing for the slide 11. In this case a number of air pockets 30 are formed within the slide 11 which pockets are distributed around the circumference thereof. Air is blown into each of of these air pockets 30 through air lines 31 and also through throttles 32 if desired. The air lifts the slide 11 against the force I, which is produced by the leaf springs 14. A gap f is thus formed, through which the air escapes. The throttles 32 and the gap f between slide 11 and guide rail 7 thus form a kind of bridge circuit which automatically regulates the pressure in the pockets 30. Instead of the throttles 32, the lines 31 can be made so thin that they have the desired throttling effect.

To enable the slide 11 to adapt itself to any surface inclination of the guide rail 7, it is desirable to provide the swivel joint 13 between the sensor holder 12 and the slide 11 (FIGS. 1 and 2).

Figure 6:
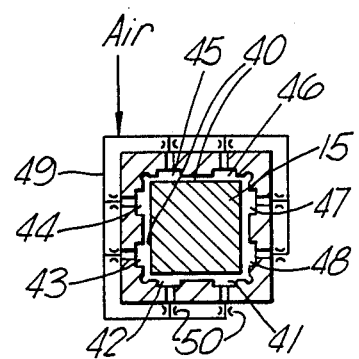
Figure 7:
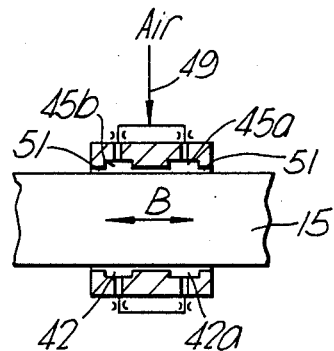

The mounting of the drive beam 15, which has, for example, a square cross section and four bearing surfaces 40, can best be in the form of air bearings. FIGS. 6 and 7 show such a system. The bearing here represented is not a lifting air bearing biased by a spring, but a pneumostatic bearing in which air pockets 41 to 48 are disposed side-by-side and lengthwise over each bearing surface 40. In this system the drive beam 15 is floatingly guided by its bearing surfaces 40 between the confronting air pockets, e.g., 44 and 47, or 42b and 45b. Compressed air is supplied through throttles 50 and lines 49 to the air pockets 41 to 48. The throttles 50 and gaps 51 again form, as described in conjunction with FIG. 5, a kind of bridge circuit, which is self-centering. By the mounting here represented, the drive beam 15 is held in five of the six possible degrees of liberty. The system for the movement of the sensors can move only in the direction of the arrows B in FIG. 7 and B1 in FIG. 3.

Instead of the air bearing according to FIGS. 5 to 7, similar hydraulic bearings operating with a fluid under pressure can be used. Also, it is possible to use other supporting means or guides, such as roller guides for example.

Figure 8:
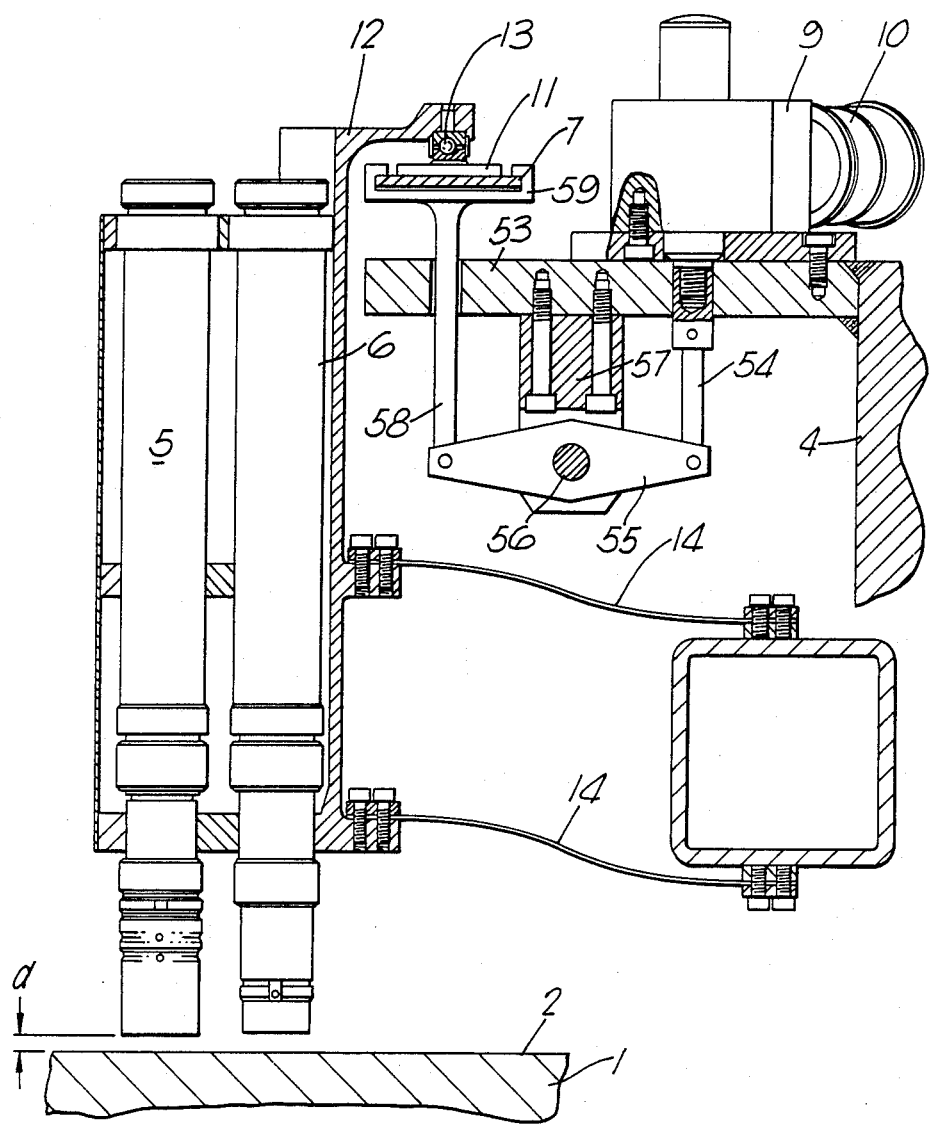
FIG. 8 is a cross section taken through a preferred embodiment of the surface test apparatus of FIGS. 1 to 3.

A preferred embodiment of the surface test apparatus, especially of the support of the guide rail 7, is represented in cross section in FIG. 8. Accordingly, the casing 4 has a supporting arm 53 extending transversely over the test body 1, and the jacks 9 and the driving means 10 in the form of worm drives, for example, are mounted on the upper side of the casing.

Each jack 9 acts on a rod 54 passing through and mounted for displacement in the supporting arm 53, the free end of the are being articulated to one arm of the lever 55. The lever 55 is pivotally mounted at its center on a pivot pin 56 fastened to a support 57 fastened to the underside of the supporting arm 53. The other arm of the lever 55 is pivotally articulated to a rod 58 which is disposed parallel to rod 54 and is mounted for displacement in a bore in the supporting arm 53. On the end of rod 58 projecting from the top of the supporting arm 53 there is fastened a shackle 59 which clamps around the guide rail 7. A plurality of such shackles with parts 9, 10 and 54 to 58 are provided lengthwise of the guide rail 7, and each shackle 59 forms one of the points of support 8 represented in FIGS. 1 and 2. Each drive means 10 is provided with a control amplifier 17 in accordance with FIG. 1. The rest of the parts are provided with the reference numbers seen in FIGS. 1 to 3.

If difference occurs between the set value and the found value at any one of the distance sensors 6, adjusting signals are fed to the drive system 10. The rod 54 is thus moved backward or forward in the direction of the surface 2 of the test body 1, while at the same time the rod 58 is moved backward or forward in the opposite direction. The combination of parts 54, 55 and 58 is only a reversing mechanism. By the movement of the rod 58 and the section of the guide rail 7 fastened thereto is likewise moved accordingly relative to the surface 2 and therefore adjusted such that the desired change in distance is achieved. Since the guide rail 7 is held clamped by the shackles 59, the rail sections held thereby accompany every movement of the rod 58 in both of the possible, opposite directions, regardless of which positions the next adjacent shackles 59 or sections of the guide rail assume.

The invention is not limited to the described embodiment, which can be modified in many ways. This applies especially to the driving and control means represented, but also, for example, to the device producing the reciprocating movement of the sensor holder and to the nature of the sensors 5 and 6. The embodiment represented in FIG. 8 might therefore be modified by biasing the guide rail downwardly toward the support arm 53 by means of a biasing mechanism. In this case, the reversing mechanism formed by parts 54, 55 and 58 would be operated so as to thrust only, which permits a simple upward and downward movement of the guide rail 7 with no free play. If instead of the square drive beam 15 a beam of circular cross section is selected, it is best also to provide a special anti-rotating device for the beam.

I claim:

1. In a surface testing apparatus having a sensor for testing a surface having a contour: a sensor holder for holding said testing sensor, means for moving said sensor holder along a preselected path of movement over and at a preselected distance from said surface, said means for moving said sensor holder having a flexible guide rail for establishing said path of movement and for guiding said sensor holder during movement thereof; and means for automatically shaping said guide rail to have a contour matching the contour of said surface, such that said distance is maintained substantially constant during testing of said surface by said testing sensor, said shaping means including a distance sensor means for measuring actual distances between said guide rail and said surface at a plurality of points along the path of movement and means coupled to said distance sensor means for adjusting the distance of said guide rail from said surface at said points to said preselected distance.

2. A surface testing apparatus according to claim 1, wherein said guide rail is resiliently flexible, and wherein said adjusting means comprises means for supporting the guide rail along the path of movement on a plurality of points of support and for increasing or decreasing the distances between said rail and said surface at any point of said points of support.

3. A surface testing apparatus according to claim 2, said distance sensor means being fastened to the sensor holder for producing actual value signals corresponding to the actual distance of said guide rail from said surface, and said shaping means further comprising a nominal value means for producing nominal value signals corresponding to nominal distances of said guide rail from said surface at said points of support, means for comparing said actual value signals and said nominal value signals and means for controlling said adjusting means during movement of said holder along said path, such that said actual value signals and said nominal value signals are substantially equal at said points of support.

4. A surface testing apparatus according to claim 1, wherein said guide rail has a guiding surface, said sensor holder rests against said guiding surface, and a biased support biasing said sensor holder against said guiding surface.

5. A surface testing apparatus according to claim 4, wherein said biased support comprises two leaf springs each having a first end fastened to a drive beam movable parallel to the path of movement, and a second end fastened to the sensor holder, to form a parallel guidance system.

6. A surface testing apparatus according to claim 4, wherein said beased support comprises a slide supported on said guide rail and a swivel joint disposed between said guide rail and said sensor holder.

7. A surface testing apparatus according to claim 6, comprising pneumatic or hydraulic lifting bearings for guiding said slide.

8. A surface testing apparatus according to claim 1, wherein said moving means comprise means for reciprocatingly moving said sensor holder along said guide rail, said means being constructed as a vibratory system having a natural frequency and including said sensor holder, and an exciter means for operating said vibratory system at or in the neighborhood of its natural frequency such that said sensor is moved over said surface with said natural frequency or with a frequency in the neighborhood thereof.

9. A surface testing apparatus according to claim 8, comprising pneumatic or hydraulic lifting bearings for guiding said vibratory system.

10. A surface testing apparatus according to claim 1, comprising a plurality of sensor holders supported on said guide rail.

11. A surface testing apparatus according to claim 10, wherein said sensor holders are coupled to a common drive beam.

12. In a surface testing apparatus having a plurality of testing sensors for testing a surface having a contour: a plurality of sensor holders each for holding one of said testing sensors, means for moving said sensor holders along preselected paths of movement over and at preselected distances from said surface, said means for moving said sensor holder having a flexible guide rail for establishing said paths of movement and for guiding said sensor holders during movement thereof; and means for automatically shaping said rail to have a contour matching the contour of said surface, such that said preselected distances are maintained substantially constant during testing of said surface by said testing sensors, said shaping means comprising a plurality of distance sensor for measuring actual distances between said guide rail and said surface at a plurality of points along the paths of movement, each distance sensor being fastened to one of said sensor holders for producing actual value signals corresponding to the actual distances of the guide rail from said surface, means coupled to said distance sensors for adjusting the distances of said guide rail from said surface at said points to said preselected distances, means for producing nominal value signals corresponding to nominal distances of said guide rail from said surface at said points, means for comparing said actual value signals and said nominal value signals and means for controlling said adjusting means during movement of said holders along said paths, such that said actual value signals and said nominal value signals are substantially equal at said points.

* * * * *